(12) United States Patent
Colpan et al.

(10) Patent No.: US 7,109,322 B2
(45) Date of Patent: Sep. 19, 2006

(54) PROCESS FOR THE DEPLETION OR REMOVAL OF ENDOTOXINS

(75) Inventors: Metin Colpan, Essen (DE); Peter Moritz, Kerpen (DE); Joachim Schorr, Düsseldorf (DE)

(73) Assignee: Qiagen GmbH, Hilden (DE)

( * ) Notice: Subject to any disclaimer, the term of this patent is extended or adjusted under 35 U.S.C. 154(b) by 388 days.

(21) Appl. No.: 10/254,845

(22) Filed: Sep. 26, 2002

(65) Prior Publication Data

US 2003/0036175 A1   Feb. 20, 2003

Related U.S. Application Data

(60) Division of application No. 09/443,091, filed on Nov. 18, 1999, now abandoned, which is a continuation of application No. 09/026,613, filed on Feb. 20, 1998, now abandoned, which is a continuation of application No. 08/687,522, filed as application No. PCT/EP95/00391 on Feb. 3, 1995, now Pat. No. 5,747,663.

(30) Foreign Application Priority Data

| Feb. 7, 1994 | (DE) | 44 03 692 |
| Jun. 25, 1994 | (DE) | 44 22 291 |
| Sep. 1, 1994 | (DE) | 44 31 125 |
| Sep. 14, 1994 | (DE) | 44 32 654 |

(51) Int. Cl.
| C07H 21/00 | (2006.01) |
| C12N 1/00 | (2006.01) |
| C12N 1/08 | (2006.01) |
| C12P 19/34 | (2006.01) |

(52) U.S. Cl. ............ 536/25.4; 435/91.1; 435/262; 435/267; 435/270; 536/25.41

(58) Field of Classification Search ........ 435/91.1, 435/262, 267, 268, 269, 270; 210/691; 536/127, 536/25.4, 41.1, 25.41
See application file for complete search history.

(56) References Cited

U.S. PATENT DOCUMENTS

| 4,997,932 A | | 3/1991 | Reardon et al. | |
| 5,136,026 A | | 8/1992 | Romisch et al. | 530/416 |
| 5,254,677 A | * | 10/1993 | Guder et al. | 435/18 |
| 5,536,645 A | * | 7/1996 | Jay | 435/32 |
| 5,747,663 A | * | 5/1998 | Colpan et al. | 536/25.4 |
| 5,843,707 A | * | 12/1998 | Larsen et al. | 435/69.1 |
| 5,981,235 A | * | 11/1999 | Shultz et al. | 435/184 |
| 5,981,735 A | * | 11/1999 | Thatcher et al. | 536/25.4 |
| 6,011,148 A | * | 1/2000 | Bussey et al. | 536/25.4 |
| 6,194,562 B1 | * | 2/2001 | Smith et al. | 536/25.41 |
| 6,206,931 B1 | * | 3/2001 | Cook et al. | 623/23.75 |
| 6,235,892 B1 | * | 5/2001 | Demmer et al. | 536/25.4 |
| 6,268,492 B1 | * | 7/2001 | Mittelstaedt et al. | 536/25.4 |

FOREIGN PATENT DOCUMENTS

| EP | 83 23220 | 1/1983 |
| WO | 93/11221 | 6/1993 |

OTHER PUBLICATIONS

Aida et al J. Immunic. Methods 132 (1990)191-195.*
Schorr et al "Gene Ther" (1994)1, SUPPL. 2, S7.*
Computer Caplus Abstract 1992:54910 Morita "Cesium chloride-purified DNA in record time" 1992.*
Computer Medline 92134785 Ward et al "Rapid removal of cesium chloride from DNA obtained from ultracentrifuge gradients" "BIOTECHNIQUES" (1992) Jan. 12 (1) 76.*
Computer Derwent Abstract ep 322880 Toray Jul. 1989.*
Computer Biotechds JP 03030670 Toray Feb. 1991.*
Computer Biosis AN1982:60884 Zakian 21st Annual Meeting of the Amer Soc. for Cell Biol. USA Nov .9-13, 1981.*
Computer Caplus Abstract AN187:612903 Isa et al "J. Cell Sci" (1987) 88 (2) 219-24.*
Computer Caplus Abstract AN1993:33680 Araki et al "Yoshoku Kenkyusho Kenkyu Hokoku" (1991) 20 1-9.*
Computer Genbank.rtm Acc.No. MN20980 CA 141159-52-6 DNA Linear Black et al J.Biol. Chem 263, 9437-9942 (1988) Apr. 1993.*
Computer Genbank .RTM AH002278 DNA , Linear Apr. 1993 Chong et al "FEBS Lett." 192 47-52(1985).*
SIGMA Chemical Company 1991 Catalogue D5401 PHI X174 Phage DNA (RF-1) p. 1267.*
SIGMA Chemical Company 1991 Catalogue DNA from Calf Thymus page p. 1269.*
SIGMA Chemical Companyh 1991 Catalogue DNA from Human Placenta.*

* cited by examiner

Primary Examiner—Herbert J. Lilling
(74) Attorney, Agent, or Firm—Jacobson Holman PLLC

(57) ABSTRACT

A process for the depletion or removal of endotoxins from preparations containing active ingredients designated for therapeutical use which are obtained from natural sources by genetic engineering and/or biotechnology by treatment with chromatographic material wherein
  said natural source are lysed, the fractions obtained are optionally centrifuged, filtrated or treated with affinity chromatographic methods;
  said fractions are preincubated with an aqueous salt solution and detergents, treated with anion exchange material and then washed with another salt solution, and the active ingredients are eluted from the anion exchanger, followed by further purification in a per se known manner.

3 Claims, No Drawings

PROCESS FOR THE DEPLETION OR REMOVAL OF ENDOTOXINS

This is a Divisional of application Ser. No. 09/443,091 filed Nov. 18, 1999 now abandoned, which is a continuation of Ser. No. 09/026,613 filed Feb. 20, 1998 now abandoned, which is a continuation of Ser. No. 08/687,522 filed Sep. 30, 1996, now U.S. Pat. No. 5,747,663, which is a 371 of PCT/EP95/00391 filed Feb. 3, 1995.

The present invention pertains to a process for the depletion or removal of endotoxins from preparations containing active ingredients designated for therapeutical use which are obtained from natural sources by genetic engineering and/or biotechnology by treatment with chromatographic material, as well as the use thereof, an aqueous solution for performing said process, and a kit containing members for performing said process.

Molecular biological processes are increasingly gaining importance in the preparation of medicaments. They include, on one hand, the classical genetic engineering methods for the preparation of medicaments, and also, to a growing extent, the so-called gene therapy in which nucleic acids are introduced in the genome of species to be treated. The removal of endotoxins is becoming of crucial importance therein.

For example, to prepare plasmid DNA on a preparative scale, it is necessary to proliferate the plasmids by means of so-called host cells. These are generally gram-negative enterobacteria, such as mutants of *E. coli* K-12. Gram-negative bacteria have cell walls which are surrounded by an outer membrane. Located on this membrane are so-called lipopolysaccharids (LPS), also known under the designation endotoxins. Endotoxins are responsible, for instance, for the typical phenomena which accompany a bacterial intoxication, such as inflammatory reactions and fever as well as endotoxic shock.

As noted in German Patents P 44 03 692 and P 44 22 291, in vivo and ex vivo gene therapy involves the use of plasmid DNA for the treatment of genetically caused diseases, such as cystic fibrosis, but also for the treatment of cancer or hemophilia, or for the immunisation against infectious diseases (TIBTECH, Special Issue: Gene Therapy Therapeutic Strategy and Commercial Prospects, May 1993, Vol. 11, No. 5 (112)). It is of crucial importance therein that the administered DNA cause no side-reactions, such as inflammatory or necrotic reactions. It must be ensured, therefore, that the DNA used for such kind of treatment is not contaminated with endotoxins.

Preparations made by genetic engineering and/or biotechnology may also contain endotoxins. Therefore, it is important to remove or deplete the endotoxins to below physiologically safe amounts.

The purification methods presently known, for example, for plasmid DNA from gram-negative bacteria, are not able to completely remove the endotoxins from plasmid DNA. These methods include, for instance, cesium chloride gradient centrifugation or anion exchange chromatography.

Cesium chloride gradient centrifugation is based on the fact that differently sized DNA molecules have different migration velocities in a salt gradient. However, lipopolysaccharides show the same migration bevahior as DNA in a density gradient and thus cannot be effectively separated from DNA.

As compared to anion exchange chromatography, cesium chloride gradient centrifugation is rather time-consuming and uses a number of toxic substances, such as ethidium bromide. Also, cesium chloride has to be removed by an additional dialysis.

Aida and Pabst, in "Removal of endotoxin from protein solutions by phase separation using Triton X 114", J. Immunol. Methods 132, 191–195 (1990), suggest a method for the removal of endotoxins from protein solutions by means of Triton X 114 extraction. The solution to be treated is spiked with the detergent Triton X 114. The protein-containing aqueous phase is removed following incubation and centrifugation, and the endotoxin-removed or endotoxin-depleted protein is precipitated. As has already been suggested in P 44 03 692, this method may also be used for the extraction of endotoxins from DNA solutions. However, this method is characterized by by a rather high expenditure of work and is applied only after the isolation of the DNA. This method is less suited for the purification of DNA quantities on a preparative, especially industrial, scale.

The object of the invention is to provide a process which is successful in preparing endotoxin-free or endotoxin-depleted preparations containing active ingredients designated for therapeutical use which are obtained from genetic engineering and/or biotechnological sources. The process according to the invention is to avoid the drawbacks described above. The purification of the DNA and the separation or depletion of the endotoxins are to be performed in the same process or process step.

This object is achieved by a process having the features as defined in claim 1. Subclaims 2 to 7 pertain to preferred embodiments of the process according to the invention. Claim 8 pertains to the use of an anion exchanger for the depletion or removal of endotoxins from preparations containing nucleic acids.

In the process according to the invention, the natural sorces from which the preparations containing active ingredients designated for therapeutical use are obtained by genetic engineering and/or biotechnology are first lysed. This lysing is preferably performed according to per se known methods, such as alkaline lysis, but also by other lysis methods, such as the application of high pressure (French Press), boiling lysis, or the use of detergents or lysozyme. The material obtained by the alkaline lysis is optionally freed from coarse cell debris by centrifugation or filtration steps.

According to the invention, before the actual purification process, for example, by means of conventional anion exchange chromatography, the "cleared lysate" (cL), which has been obtained, for instance, by alkaline lysis, is subsequently filtrated according to the procedure suggested in P 44 32 654 and then preincubated with certain salt/detergent combinations.

The German Patent Application 44 32 654.8 suggests a process and a device for the isolation of cell contents, such as nucleic acids, from natural sources. The filtration method described therein for the preparation of nucleic acids proceeds from the lysis of the nucleic acid containing sources, the lysate is kept standing for some time, the resulting lysate passes a filter layer of glass, silica gel, alumina or packed diatomaceous earth, or interlaced or bonded non-wovens of fiber glass and silica gel, as well as cellulose, paper, pressed paper, non-wovens made of paper and particles or sheets, membranes or plastics, such as polypropylene-based non-woven fabrics, then the fraction leaving the filter layer is collected and subsequently the nucleic acid is further processed from the collected fraction The filter layers may be modified such that no affinity to the nucleic acid exists, in particular by minerals bearing hydroxyl groups or coated minerals, especially diol silica gel, diol diatomaceous earth, and/or diol perlite. This may be done under such conditions where silica gel has no affinity to nucleic acids. A preferred device for performing the process suggested in P 44 32 654.8 preferably has a cylindrical hollow body with a filtration means arranged therein. In particular, the filter layer consists of a packed layer of diatomaceous earth having a particle size in the range of from 5 µm to 500 µm at a total thickness the filter layer of from 0.1 to 200 mm. It may be advantageous then to arrange an additional layer in the hollow body, namely above and/or below the diatomaceous earth layer, which prevents premature permeation in the filter of the solution to be filtered or the outflow of the solution from the suggested device.

The device suggested in P 44 32 654 can advantageously be combined with other instruments useful for the preparation of nucleic acids, such as disclosed in P 31 39 664.

P 41 27 276 discloses anion exchangers embedded in a membrane (3M Empore membrane). Such systems are available under the designation of QIAWELL.

As incubation solutions, there may be used, for instance, salt solutions of sodium chloride, potassium chloride, guanidinium ochloride, sodium perchlorate, and other chaotropic salts.

As detergents, there may be used, in particular, such as NP 40, Tween 80, Tween 20, Triton X 100, Triton X 114, Syperonic F-68, or other non-ionic detergents. The detergents are preferably present in concentrations of from 0.1% to 30%. The salt solutions usually have ionic strengths corresponding to that of an 0.1–2.0 M NaCl solution.

The filtrated lysate may also be incubated with an affinity-chromatographic material. This may be, in particular, a chelating agent bound to silica gel. Affinity materials, such as silica surfaces modified with NTA (nitrilotetraacetate) or IDA (imino-diacetate) have proven to be useful. On this affinity support, nickel ions, for example, are complexed which may interact with side-chain nitrogen containing amino acid residues in proteins through additional coordination sites. The filtrated lysate may be incubated, in particular, with Ni/NTA chromatographic material based on silica gel. The chromatographic material may be centrifuged off, for instance, after the incubation is completed, if batch-mode was used, and the supernatant may be further purified through anion exchangers or other materials. In addition to batch mode, operating in columns may also be performed if the sample condition allows.

The anion exchanger is preferably a material based on a polymeric inorganic support material, such as acrylic resin, dextrane, agarose or combinations thereof, wherein the groups bound to the anion exchanger have a surface charge of from 1 to 4 µM/m² of support surface area, corresponding to 0.5 to 500 µM/ml. The chromatographic support material suggested in P 44 03 692 may preferably be used as a modified porous or non-porous inorganic and/or organic material. Further, anion exchange materials, such as QIAGEN®, DEAE Sepharose®, Q Sepharose, DEAE Sephadex®, Poros 20 M/P and/or Poros 50 M/P may be used following the treatment for the removal of endotoxins.

Following the process according to the invention for the removal or depletion of endotoxins, the DNA may also be further purified over inorganic materials, such as silica gel, diatomaceous earth, glass, alumina, titania, hydroxyapatite, or inorganic materials, such as agarose, dextrane, acrylic amide, polystyrene resins, and copolymers of the monomeric building blocks of the monomers mentioned.

In particular, active ingredients, such as nucleic acids, for example, plasmid DNA, can be obtained free of endotoxins with the process according to the invention. In addition, nucleic acids such as RNA, YACs or genomic DNA having sizes of from 6 bp to 1000 kbp can be obtained free of endotoxins. As the natural sources from which the nucleic acids or the ingredients for therapeutical use, for example, are obtained, there may be mentioned, for instance, cells, cell organells, tissues or microorganisms.

Also, protein solutions or virus particles, such as adenoviruses, AAV or retroviruses, can be freed from endotoxins or depleted of their endotoxin content by the process according to the invention.

The preincubation of the "cleared lysate" is preferably performed with salt solutions containing alkali halogenide salts, non-ionic surfactants, and buffer substances. The alkali halogenide concentration corresponds to an ionic strength such as that of NaCl of a concentration of from 0.1 to 2.0 M.

The fractions thus treated are contacted with the chromatographic material to adsorb the active ingredients at the support surface. Salt solutions containing alkali halogenide, such as sodium chloride, potassium chloride, lithium chloride etc., are preferably used. The ionic strength of the washing solution approximately corresponds to that of an NaCl solution of 0.5 to 2.0 M.

The process according to the invention ensures the depletion or removal, in a surprisingly simple way, of endotoxins from preparations containing active ingredients designated for therapeutical use which are obtained from natural sources by genetic engineering and/or biotechnology. Surprisingly, the preincubation with salt/detergents results in a separation of the endotoxins without adversely affecting the yield and purity of the plasmid DNA in the subsequent chromatographic purification.

The invention will be illustrated in more detail by the following examples.

The buffers, which are abbreviated P1, P2, P3, QBT, QC and QN in the following, have the following composition:

| | |
|---|---|
| P1 | 10 µg/ml RNase A, 50 mM Tris/HCl, 100 mM EDTA |
| P2 | 200 mM NaOH, 1% SDS |
| P3 | 3 M KAc, pH 5.5 |
| QBT | 750 mM NaCl, 50 mM MOPS, 15% alcohol*, pH 7.0, 0.15% Triton X 100 |
| QC | 1.0 M NaCl, 50 mM MOPS, 15% alcohol, pH 7.0 |
| QN | 1.6 M NaCl, 50 mM MOPS, 15% alcohol, pH 7.0 |

*As the alcohols, isopropanol or ethanol are preferably used.

EXAMPLE 1

Purification of 100 mg of Endotoxin-Free pUC18 DNA by means of Anion Exchange Chromatography A 10 l fermenter culture of the plasmid pUC18 is centrifuged, and the resulting bacterial pellet is resuspended with 500 ml of buffer P1, and alkaline lysis is performed by the addition of 500 ml each of buffers P2 and P3. Cell debris, genomic DNA and SDS precipitates (SDS=sodium dodecyl sulfate) are separated off using a filtration unit, such as proposed, for example, in P 44 03 692.

To the "cleared lysate (cL)", there is now added ¹⁄₁₀ of its volume (150 ml) of an endotoxin removal buffer (750 mM NaCl/10% Triton X 100/50 mM MOPS, pH 7.0) and mixed with the cL. The mixture is incubated at 4° C. for one hour and subsequently pumped onto an anion exchange column having a diameter of 4.4 cm and a length of 50 cm by means of a peristaltic pump at a flow rate of 4 ml/min. The column had previously been equilibrated with 350 ml of QBT buffer (10 ml/min). The column is washed with 2.5 l of QC (15 ml/min). The plasmid DNA is eluted with 400 ml of QN buffer (3 ml/min) and subsequently precipitated with 0.7 volumes of isopropanol and then washed with 70% ethanol.

The determination of the endotoxin content is performed by Biowhittaker LAL test. The purified DNA can be injected directly as a genetic vaccine into muscle or other tissues.

After endotoxin depletion, the DNA has endotoxin contaminations of only<50 I.U./mg of DNA.

TABLE

Endotoxin Content in DNA Preparations before and after the Application of the Process According to the Invention.

| DNA Prep. | Endotoxin content in I.U./mg of DNA | |
|---|---|---|
| | before | after |
| 1 | 2500 | 10 |
| 2 | 4200 | 17 |
| 3 | 3300 | 15 |
| 4 | 2900 | 15 |
| 5 | 3900 | 12 |

EXAMPLE 2

Purification of 10 mg of Endotoxin-Free pBR322 DNA by means of Anion Exchange Chromatography A 5 l shake culture of the plasmid pBR322 is centrifuged, and the resulting bacterial pellet is resuspended with 125 ml of buffer P1, and alkaline lysis is performed by the addition of 125 ml each of buffers P2 and P3. Cell debris, genomic DNA and SDS precipitates are separated off by centrifugation. The lysate is then cleared over a folded filter.

To the cL, there is added 1/10 of its volume (35 ml) of a buffer consisting of 20% NP 40, 750 mM NaCl, 50 mM MOPS, pH 7.0, and incubated with the cL mixture at 4° C. for one hour. The DNA is then isolated as follows: The pretreated cL is charged onto a QIAGEN tip 10,000 anion exchange column. After the cL has flown through, the column is washed with the buffer QC, and the DNA is subsequently eluted with buffer QF (1.25 M NaCl, 50 mM Tris/HCl, 15% ethanol, pH 8.5). The DNA thus prepared can be coupled to recombinant adenovirus particles. The adenovirus/DNA complex obtained may then be used for in vivo or ex vivo gene therapy.

The biomass of a 20 l fermenter culture of the plasmid pUC19 is lysed by the addition of 1 l each of the buffers P1, P2, P3 and subsequently filtered over a diatomaceous earth packing arranged in a column. To the filtrated lysate is added 20 g of Ni-NTA modified silica gel, followed by incubation at RT on a shaker for 30 min. Subsequently, the Ni-NTA modified silica gel is separated off by centrifugation, and the supernatant further purified over an anion exchange chromatographic column.

The invention claimed is:

1. A composition comprising, in aqueous solution, an alkali halogenide at concentrations of 0.2–2.0 M, a non-ionic surfactant in amounts of 0.1–30%, and MOPS at a concentration of 10–100 mM.

2. The composition of claim 1, wherein the alkali halogenide is NaCl, KCl, or lithium chloride.

3. The composition according to claim 1, wherein the alkali halogenide is one or more of sodium chloride, potassium chloride, guanidinium chloride, sodium perchlorate, or other chaotropic salt, and the non-ionic detergent is one or more of Triton X114, Triton X100, NP40, Tween 20, Tween 80, or Syperonic F-68.

* * * * *